United States Patent
Wurm

(10) Patent No.: US 12,134,500 B2
(45) Date of Patent: Nov. 5, 2024

(54) METHOD FOR PROTECTING TUBING

(71) Applicant: Single Use Support GmbH, Kufstein (AT)

(72) Inventor: Thomas Wurm, Stumm (AT)

(73) Assignee: SINGLE USE SUPPORT GMBH, Kufstein (AT)

( * ) Notice: Subject to any disclaimer, the term of this patent is extended or adjusted under 35 U.S.C. 154(b) by 33 days.

(21) Appl. No.: 17/545,427

(22) Filed: Dec. 8, 2021

(65) Prior Publication Data
US 2022/0185538 A1 Jun. 16, 2022

(30) Foreign Application Priority Data

Dec. 16, 2020 (EP) ..................... 20214528

(51) Int. Cl.
| | |
|---|---|
| *A61M 39/18* | (2006.01) |
| *A61J 1/14* | (2023.01) |
| *B65D 23/08* | (2006.01) |
| *B65D 77/06* | (2006.01) |

(52) U.S. Cl.
CPC ............ *B65D 23/0885* (2013.01); *A61J 1/14* (2013.01); *B65D 77/06* (2013.01)

(58) Field of Classification Search
CPC ........ B65D 23/0885; B65D 77/06; A61J 1/14; A61J 1/16; A61M 39/1011; A61M 39/10; A61M 39/165
USPC ......................................... 215/12.1; 604/6.16
See application file for complete search history.

(56) References Cited

U.S. PATENT DOCUMENTS

| | | | |
|---|---|---|---|
| 4,596,571 A | * | 6/1986 | Bellotti .............. A61M 39/1011 |
| | | | D24/129 |
| 5,100,394 A | | 3/1992 | Dudar et al. |
| 5,135,489 A | | 8/1992 | Jepson et al. |
| 5,158,554 A | | 10/1992 | Jepson et al. |
| 5,167,648 A | | 12/1992 | Jepson et al. |
| 5,171,234 A | | 12/1992 | Jepson et al. |
| 5,188,620 A | | 2/1993 | Jepson et al. |
| 5,211,638 A | | 5/1993 | Dudar et al. |
| 5,411,499 A | | 5/1995 | Dudar et al. |
| 5,658,260 A | | 8/1997 | Desecki et al. |
| 5,797,897 A | | 8/1998 | Jepson et al. |
| 5,871,500 A | | 2/1999 | Jepson et al. |
| 5,899,888 A | | 5/1999 | Jepson et al. |
| 5,964,785 A | | 10/1999 | Desecki et al. |

(Continued)

FOREIGN PATENT DOCUMENTS

| | | |
|---|---|---|
| KR | 10-2008-0090396 | 10/2008 |
| NL | 8501555 | 12/1986 |

(Continued)

*Primary Examiner* — Elizabeth J Volz
(74) *Attorney, Agent, or Firm* — Wenderoth, Lind & Ponack, L.L.P.

(57) ABSTRACT

A method is provided for protecting tubing protruding from a container, in particular a bottle, containing a pharmaceutical fluid. The method includes providing the container filled with the pharmaceutical fluid, from which the tubing protrudes, and providing a layer of foam and/or a body of foam surrounding the tubing, preferably in its entirety, with a shell such that the layer of foam and/or body of foam is interposed between the tubing and the shell. A body of the container remains outside of the shell, attaching the shell to the container, and freezing the container and the shell surrounding the tubing.

11 Claims, 10 Drawing Sheets

(56) References Cited

U.S. PATENT DOCUMENTS

| | | | |
|---|---|---|---|
| 6,193,697 B1 | 2/2001 | Jepson et al. | |
| 6,213,996 B1 | 4/2001 | Jepson et al. | |
| 6,217,568 B1 | 4/2001 | Jepson et al. | |
| 6,261,266 B1 | 7/2001 | Jepson et al. | |
| 6,447,498 B1 | 9/2002 | Jepson et al. | |
| 6,569,125 B2 | 5/2003 | Jepson et al. | |
| 6,605,076 B1 | 8/2003 | Jepson et al. | |
| 8,603,022 B2 | 12/2013 | Lyons et al. | |
| 8,985,359 B2 * | 3/2015 | Bear | C12M 27/12 215/309 |
| 9,238,103 B2 | 1/2016 | Jakob et al. | |
| 9,867,925 B2 | 1/2018 | Lyons et al. | |
| 2001/0047154 A1 | 11/2001 | Jepson et al. | |
| 2009/0159485 A1 | 6/2009 | Jakob et al. | |
| 2010/0210990 A1 * | 8/2010 | Lyons | A61M 1/3656 604/6.16 |
| 2014/0094775 A1 | 4/2014 | Lyons et al. | |
| 2014/0100547 A1 | 4/2014 | Lyons et al. | |
| 2014/0100548 A1 | 4/2014 | Lyons et al. | |
| 2017/0189273 A1 | 7/2017 | Hsu et al. | |
| 2017/0333680 A1 * | 11/2017 | Bentley | A61M 39/165 |
| 2019/0224074 A1 | 7/2019 | Wurm | |

FOREIGN PATENT DOCUMENTS

| | | |
|---|---|---|
| WO | 2010/071812 | 6/2010 |
| WO | 2018/129576 | 7/2018 |

* cited by examiner

METHOD FOR PROTECTING TUBING

BACKGROUND OF THE INVENTION

The present invention concerns a method for protecting tubing protruding from a container, in particular a bottle, containing a pharmaceutical fluid and a protection device for tubing protruding from a container, in particular a bottle, containing a pharmaceutical fluid.

During the pharmaceutical production process, in particular the biopharmaceutical production process, fluids which occur during the (bio-) pharmaceutical production process have to be stored and/or transported in amounts which far exceed the dosages for individual patients. Since such amounts of pharmaceutical fluids represent a very large value, in the pharmaceutical industry extreme measures have to be taken in order to protect not only the sterility of the pharmaceutical fluid, but also the structural integrity of the apparatus used for storing, transporting, and further using the pharmaceutical fluid.

It should be mentioned that the containers along with the pharmaceutical fluids are frozen for transportation and storage in order to prevent unwanted (bio-) chemical processes and reactions during that time.

Solutions for protecting containers filled with pharmaceutical fluids are disclosed for example in WO 2018129576 A1. Such solutions are highly effective, in particular for flexible containers, such as single use bags.

However, there are other, more rigid containers, such as in particular bottles, which in and of themselves are strong enough to ensure the structural integrity during transportation and storing. For such containers solutions as mentioned before would be somewhat inappropriate as they would increase the size of the object to be transported or stored, without adding a significant benefit.

Containers, such as bottles, used in the pharmaceutical production process include tubes, connectors, and the like which are attached to the containers for easy access to the containers after transportation or storage, and which are vital to keep the sterility of the pharmaceutical fluid. Such tubes, connectors, and other attachment—collectively referred to as tubing in here—are in fact in need of additional protection during transportation and storage of the containers, especially because the material tubing is commonly made of in many cases becomes brittle when frozen.

SUMMARY OF THE INVENTION

The object of the present invention is therefore to provide a method and a protection device which allow for easy protection of the tubing during transportation and/or storage in a frozen state, in particular without adding unwanted volume to the object to be stored and/or transported.

Regarding the method this object is achieved with the following steps:
  providing the container filled with the pharmaceutical fluid, from which the tubing protrudes,
  providing a layer of foam and/or a body of foam,
  surrounding the tubing, preferably in its entirety, with a shell such that the layer of foam and/or body of foam is interposed between the tubing and the shell, while a body of the container remains outside of the shell,
  attaching the shell to the container, and
  freezing the container and the shell surrounding the tubing.

The protection device comprises a shell which forms a chamber for surrounding the tubing as well as a layer of foam and/or a body of foam. The protection device comprises an attachment element for attaching the shell to the container, in such a way that the tubing can be arranged, preferably entirely, inside the shell.

Protection is additionally sought for an arrangement comprising:
  a container, in particular a bottle, containing a pharmaceutical fluid,
  tubing protruding from the container,
  a protection device according to the invention which surrounds the tubing and which is attached to the container, and
  a layer of foam and/or a body of foam interposed between the tubing and the shell,
wherein the arrangement is preferably present in a frozen state.

Protection is additionally sought for the usage of a protection device according to the invention in a method according to the invention.

According to the invention the freezing of the container with the shell (and therefore of course the fluid, the tubing, and the layer of foam and/or body of foam) results not only in the protection of the pharmaceutical fluid as mentioned above, but also serves to harden the layer of foam and/or body of foam inside the shell. This hardening of the layer of foam and/or body of foam is advantageous as it immobilizes the tubing so the danger of mechanical damage (caused by impacts or scraping and the like) to the tubing is greatly reduced, and under most circumstances excluded. In this way the tubing is effectively and easily protected, while the body of the container is free of additional bulk.

The layer of foam and/or body of foam is interposed between the tubing and the shell according to the invention. This means that at least in part the layer of foam and/or body of foam is arranged between the tubing and the shell, such that the layer of foam and/or body of foam significantly reduces contact areas between the shell and the tubing.

Of course, more than one layer of foam and/or body of foam can be used according to the invention. In the following the expression "layer of foam and/or body of foam" means that also more than one layer of foam and/or body of foam can be used, unless specified otherwise. In preferred embodiments, the layer of foam and/or body of foam is disposed entirely around the tubing such that contact between the tubing and the shell is reduced or completely avoided.

The body of the container can be understood as the portion of the container which actually holds the pharmaceutical fluid. For example, if the container is a bottle, a collar of the bottle for closing the opening and in some cases an upper part of the neck of the bottle would not be part of the body of the container.

In general, the collar is understood to be a part of the container where an opening for filling and emptying the container is located and the tubing is attached to the container, in the context of the invention.

Preferably, the invention is used with pharmaceutical liquids, in particular biopharmaceutical liquids.

In the context of the invention, pharmaceutical fluids and liquids are either pharmaceuticals themselves or are fluids or liquids which occur as pre-products or intermediary products during the pharmaceutical production process (analogously for biopharmaceutical fluids and liquids).

The shell according to the invention can advantageously be manufactured by injection moulding, using for example a thermoplastic as material for the shell.

As mentioned before, in the context of the invention, tubing is understood to be tubes connectors (in particular sterile connectors) which are attached to the container and used to fill and/or empty the container, preferably in a sterile manner. Such tubes are commonly made from silicone or other materials which stay flexible for a long period of time.

The container, in particular the bottle, can for example be made of a thermoplastic, glass and/or metal. The layer of foam and/or body of foam can for example be a polyethylene foam (in particular high density polyethylene). In particular, viscoelastic foams can be used.

The method according to the invention can preferably further comprise transporting and/or storing the container and the shell surrounding the tubing, thawing the container and the shell surrounding the tubing, removing the shell as well as the layer of foam and/or body of foam, and removing contents of the container.

The shell can comprise two parts which are connected by a hinge, in particular an integral hinge, such that the shell can be opened and closed.

In such embodiments, the two parts can essentially be shaped as half shells, such that the tubing can easily be put inside the shell.

In other conceivable embodiments, a shell opening can be present which can be put over the tubing without opening of the shell, and the shell and/or the shell opening can be attached to the container and/or to the opening of the container.

Integral hinges are realised by a thin, flexible part of the shell which allows for pivoting the two parts of the shell with respect to each other by way of the flexibility of the integral hinge. Integral hinges are most commonly made of a plastic as material but can conceivably also be made of e.g. metal.

Furthermore, the attachment element can comprise two attachment element parts (engagement elements), each of which is arranged on a respective one of the two parts of the shell, preferably such that closing the shell simultaneously puts the attachment element into a closed position.

Formulated differently, in preferred embodiments the method steps of surrounding the tubing with a shell and attaching the shell to the container can be performed simultaneously by closing the shell around the tubing and a collar of the container such that the shell is attached to the container via a positive lock and/or a friction lock between the shell and the collar.

A positive lock is a type of lock where the shape (as opposed to a frictional force as in a friction lock) of different engagement elements prevents the shell from being detached from the container.

In particularly preferred embodiments, the attachment element can comprise at least one engagement element configured to engage at least one recess and/or at least one protrusion of the container, the at least one recess and/or the at least one protrusion preferably being arranged on a collar of an opening of the container.

The shell can be of substantially cylindrical base shape, the attachment element is arranged at a first base area of the substantially cylindrical base shape, and a second base area of the substantially cylindrical base shape is closed off.

It is noteworthy, that it is not absolutely necessary to close off the second base are of the substantially cylindrical base shape. The positive effect of the invention (namely protecting the tubing easily and effectively) can in some embodiments also be achieved to a large extent if the second base area is left open.

In preferred embodiments, the substantially cylindrical base shape can of course be augmented e.g. with rounded edges, closing elements for the shell, a constriction or the like.

The first and/or second base are of the substantially cylindrical base shape can particularly preferably be a circular or elliptical area. It is of course also possible to use rectangular or other polygonal base areas.

Naturally, the layer of foam and/or body of foam can be (pre-)arranged inside the shell before use. An operator can then either leave the layer of foam and/or the body of foam inside the shell and surround the tubing with the shell and the layer of foam and/or body of foam at the same time, or take out the layer of foam and/or the body of foam and apply the layer of foam and/or body of foam before (at least partly) surrounding the tubing (and the layer of foam and/or body of foam) with the shell.

The protection device according to the invention can be furnished with a seal, such that the protection device cannot be opened, or it is at least evident if tampering has occurred.

BRIEF DESCRIPTION OF THE DRAWINGS

Further details and advantages are apparent from the figures and the accompanying figure description. The figures show.

DETAILED DESCRIPTION OF THE INVENTION

Figure 1:
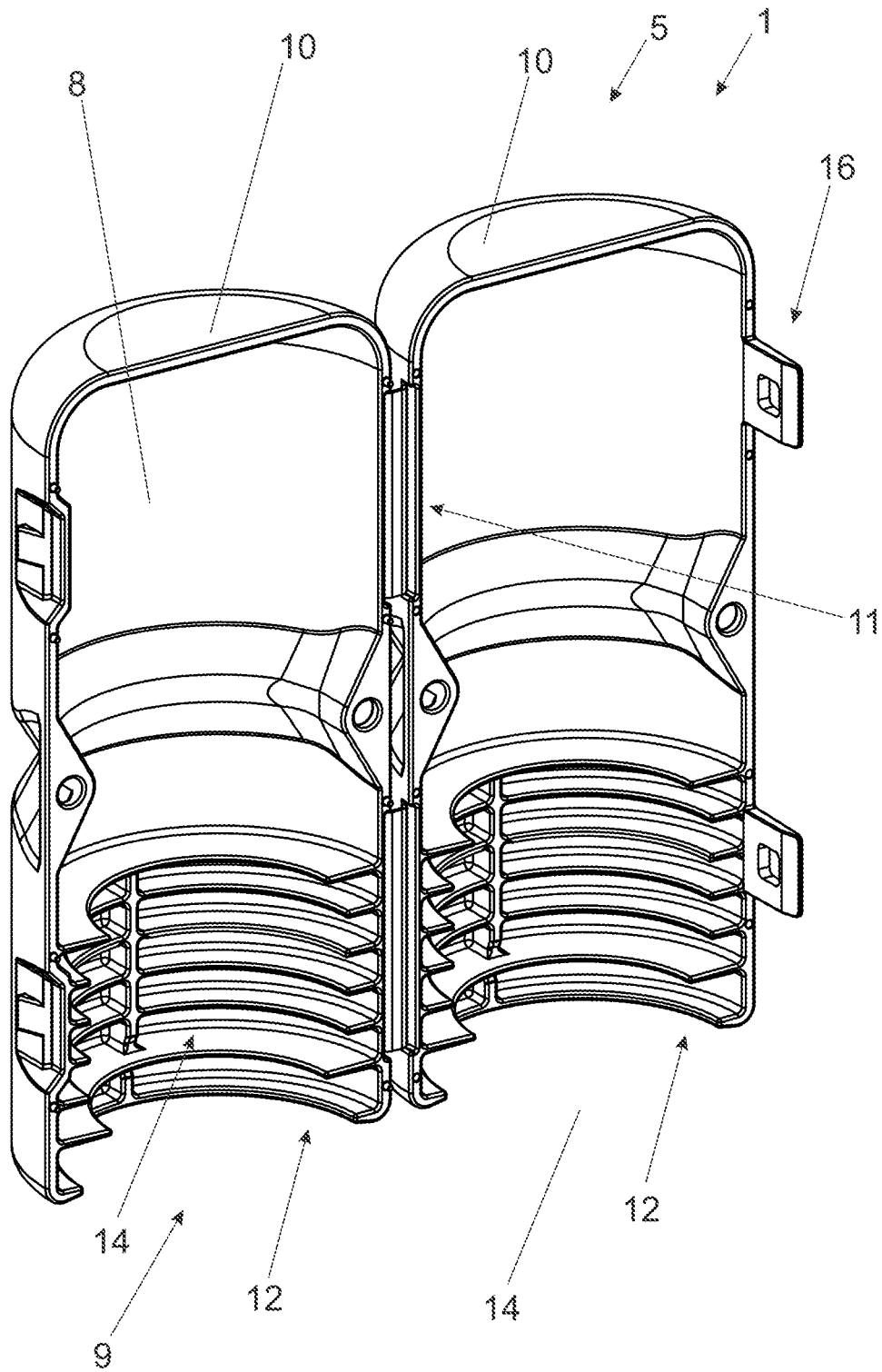
FIG. 1 an embodiment of a protection device according to the invention in an open configuration, FIG. 2 the embodiment of FIG. 1 with a body of foam arranged inside, FIG. 3 the embodiment of FIG. 1 in a closed configuration, FIG. 4 the embodiment of FIG. 1 in a closed configuration furnished with a seal, FIGS. 5 to 8 four depictions of the embodiment according to FIG. 1 visualising the method according to the invention, and FIGS. 9 and 10 two figures showing another embodiment of the protection device according to the invention.

FIG. 1 shows an embodiment of the protection device 1 according to the invention in an opened state. It comprises a shell 5 which is divided in two parts 10 in the form of half shells.

The shell is of substantially cylindrical base shape each of the two parts 10 forming half of the substantially cylindrical base shape.

Figure 3:
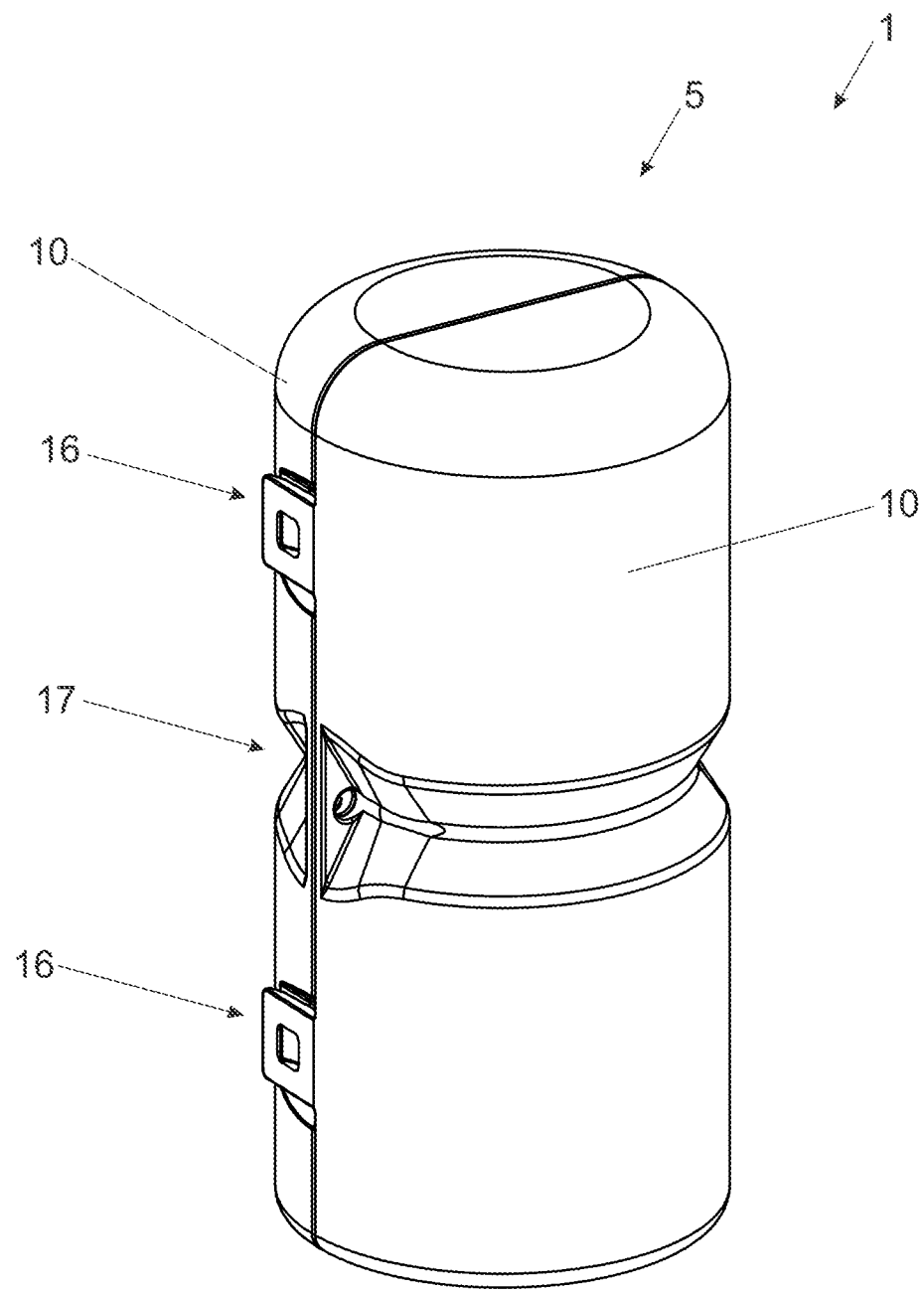

The two parts 10 of the shell 5 are connected to each other via the integral hinge 11 through which an operator can close the shell 5 (the closed position is depicted in FIG. 3).

The attachment element 9, which will be described further below, is arranged at a first base area of the substantially cylindrical base shape. A second base area of the substantially cylindrical base shape (at the top in the depiction of FIG. 1) is closed off when in the closed configuration (see FIG. 3).

Additionally, a constriction 17 of the shell 5 is present roughly halfway between the first base area and the second base area along the substantially cylindrical base shape.

Figure 2:
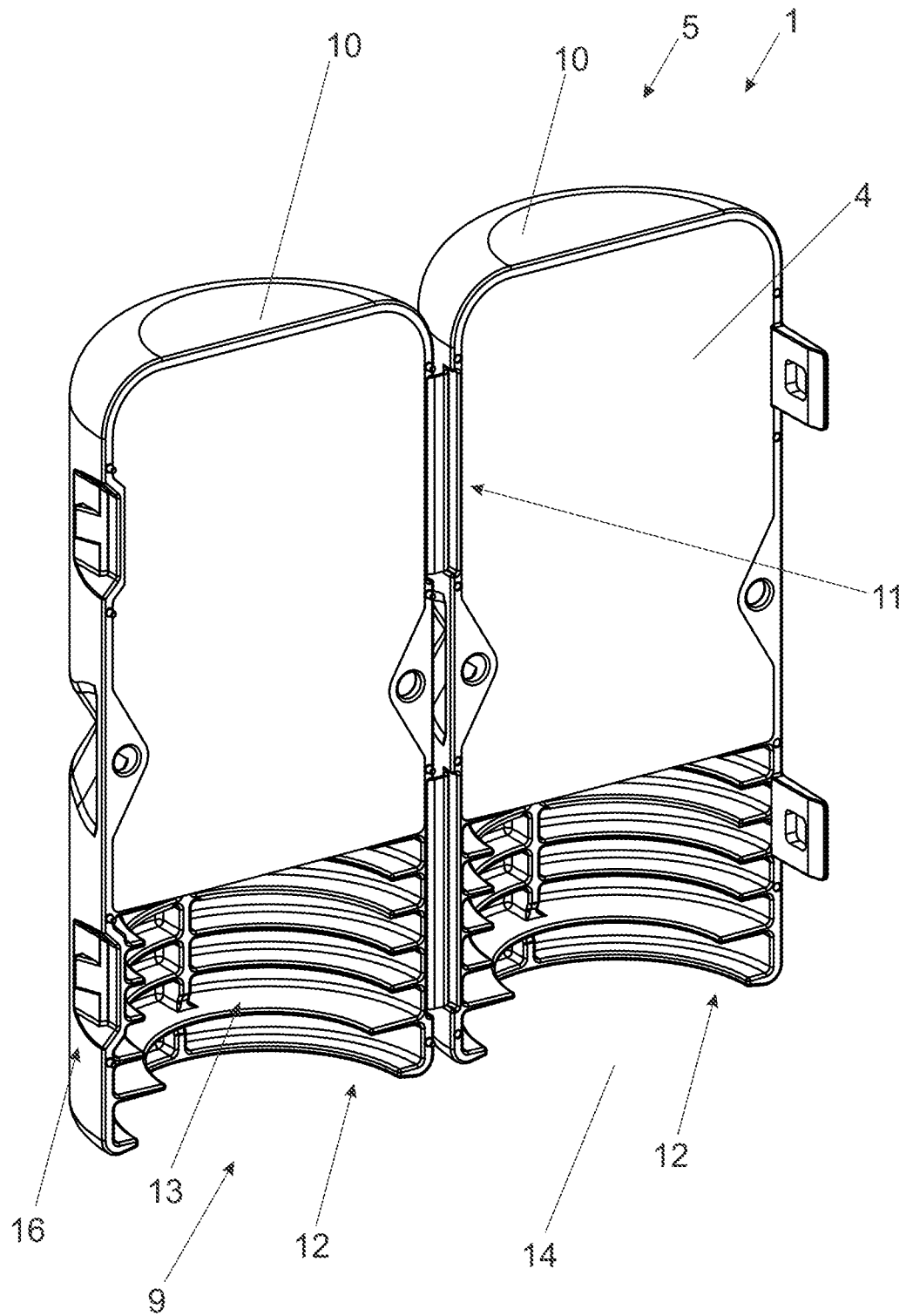

When the shell 5 is closed, the inside (generally indicated with reference numeral 8) forms a chamber in which the layer of foam 4 and/or the body of foam as well as the tubing 2 can be placed. FIG. 2 shows the embodiment of FIG. 1 with two bodies of foam 4 arranged inside each of the two parts 10.

Figure 5:
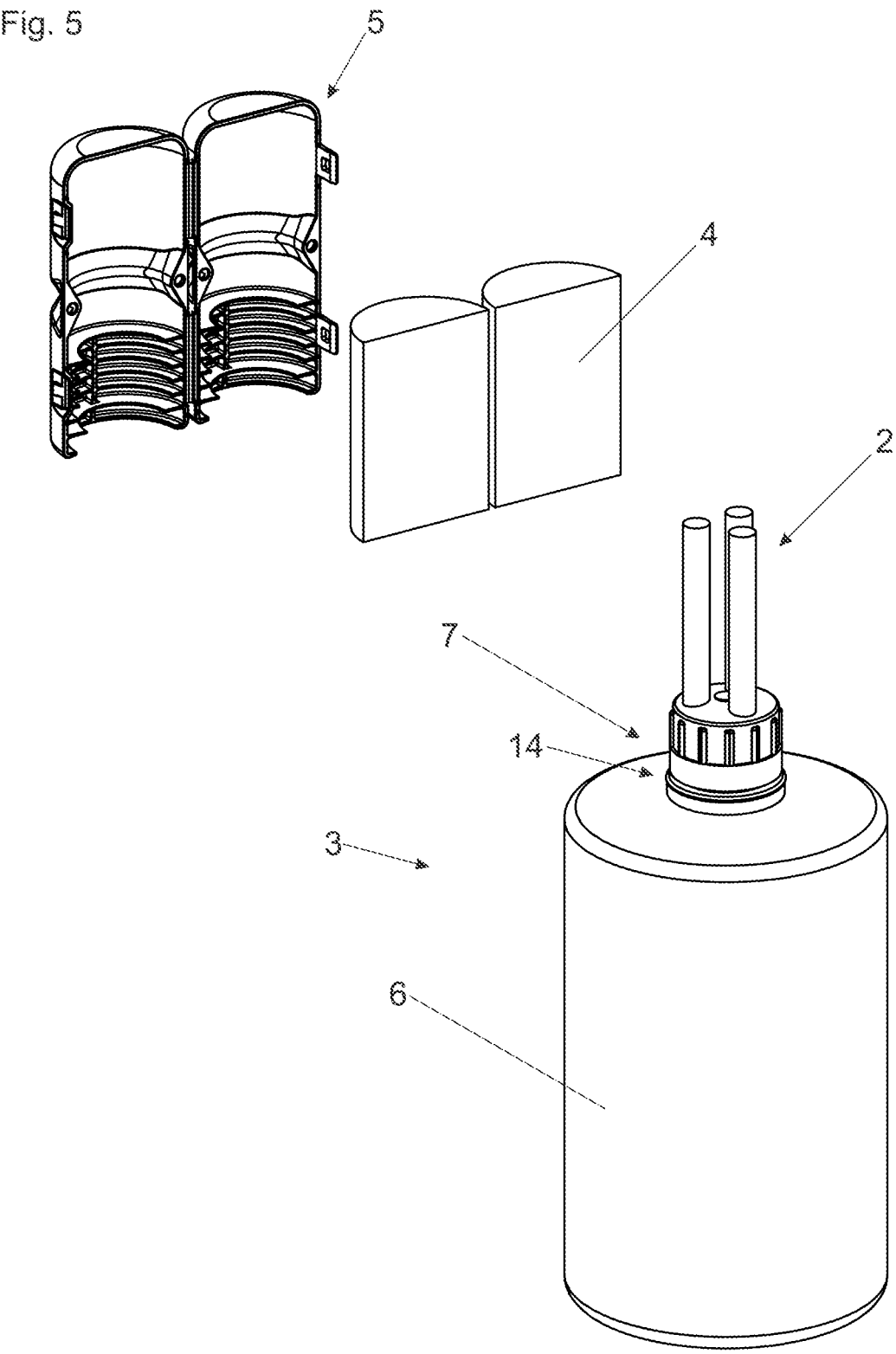

The attachment element 9 comprises engagement elements 12 in the form of recesses 13 which engage with protrusions 14 on the collar 7 of the container (see FIG. 5). Not all of the engagement elements 12 are furnished with reference numerals to avoid overburdening of the depiction.

The attachment element 9 is divided into two engagement elements (attachment element parts) 12 which are located on each of the two parts 10 of the shell 5. It is evident that closing of the shell 5 will also close the attachment element 9 in order to bring the attachment element 9 into engagement with the collar 7 (see FIG. 6 and FIG. 7).

As can be seen in FIGS. 1 and 2 there are several closing elements 16 which serve to keep the shell in the closed position. Again, not all closing elements have been furnished with reference numerals.

It can also be seen in FIG. 3 that the substantially cylindrical base shape of the shell 5 is closed off at the top (second base area of the substantially cylindrical base shape).

FIG. 3 also shows the closing elements 16 in the closed configuration.

Figure 4:
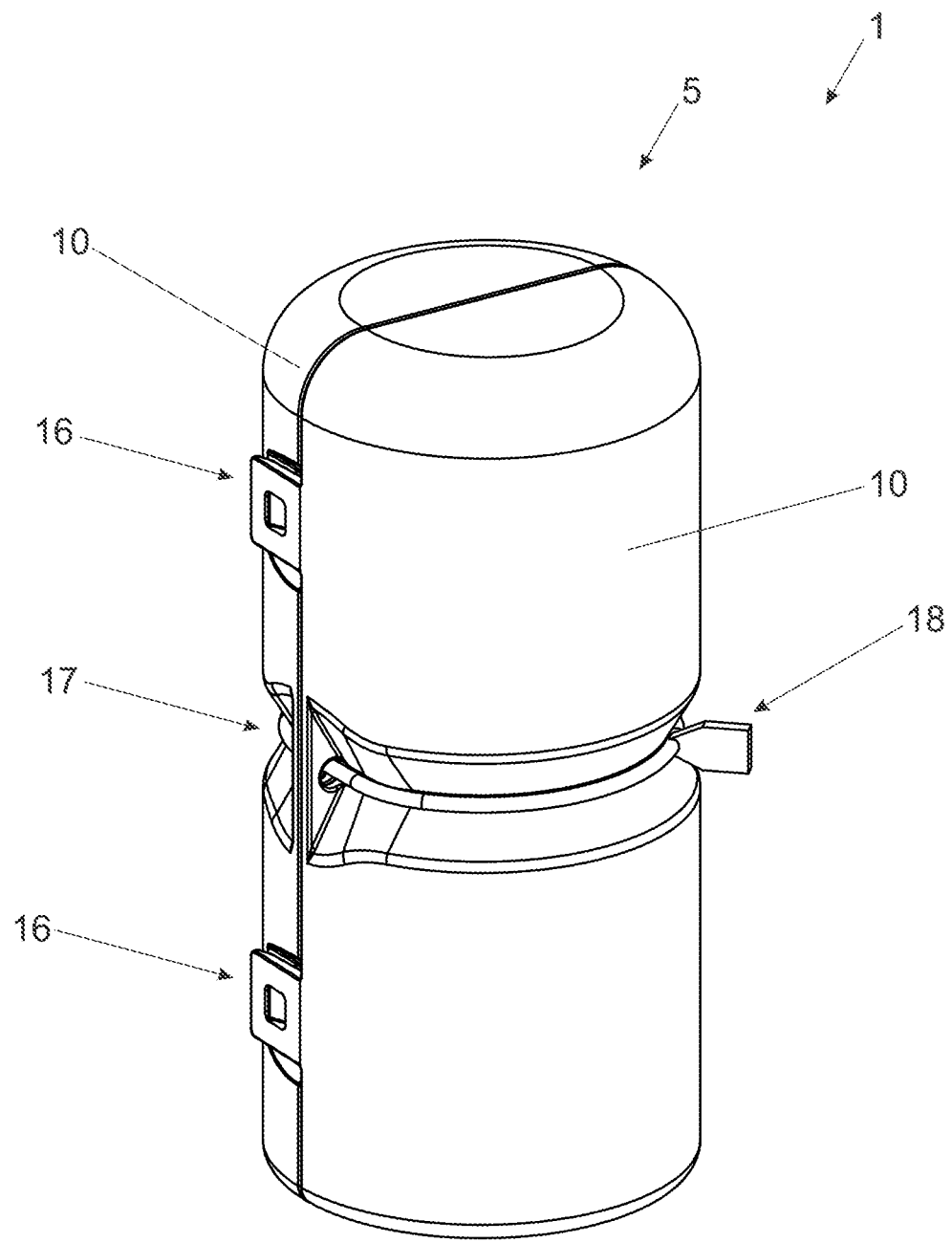

FIG. 4 shows the protection device 1 furnished with a seal 18, in this exemplary embodiment comprising a wire reaching around the constriction and a tab.

Figure 6:
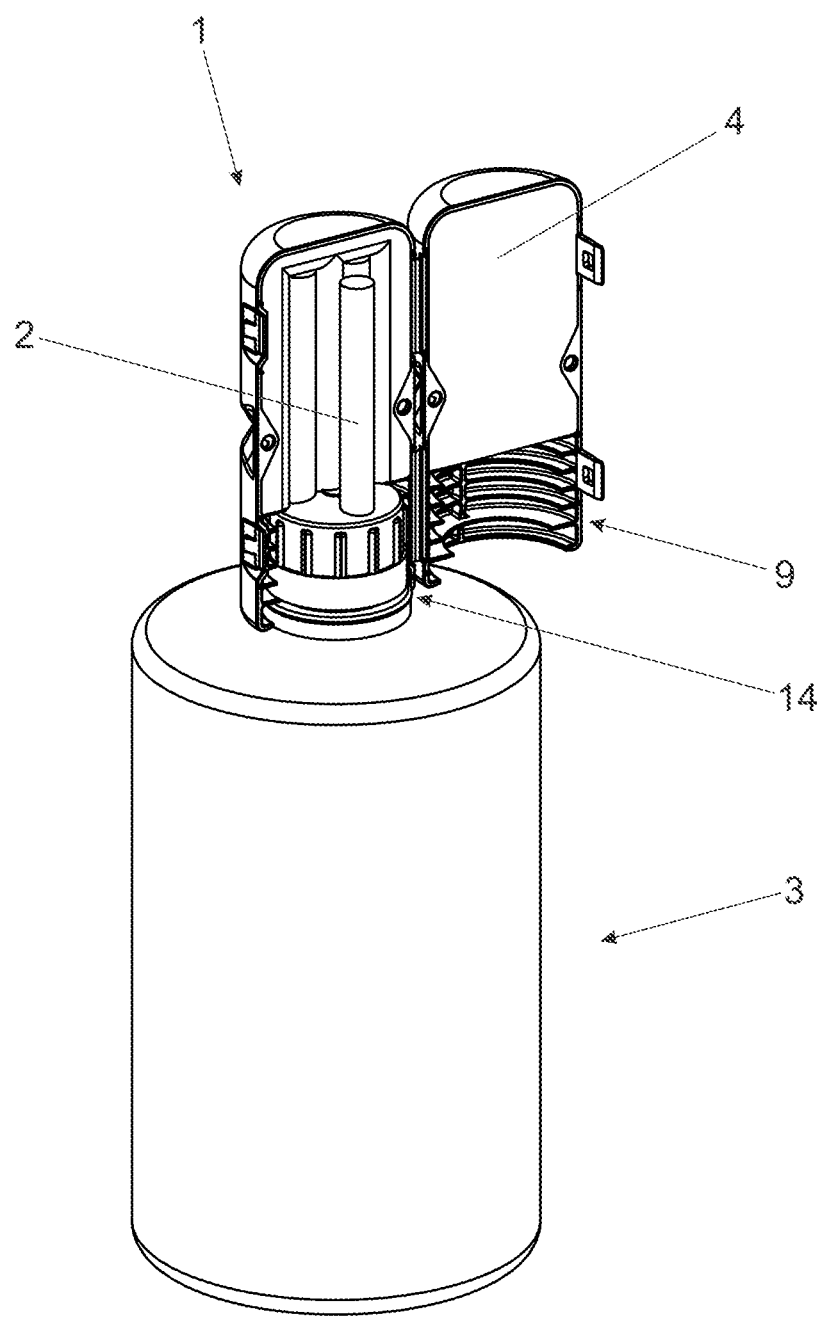

Accordingly, the constriction serves two purposes. Firstly, it acts as a guide for the seal, and secondly it tightens the layer of foam and/or body of foam 4 inside the shell 5, further immobilizing the tubing 2 (see. FIG. 6).

FIGS. 5 to 8 show an arrangement in which the protection device 1 is used for protecting the tubing 2 attached to the container 3, which is in this case a bottle. At first, the container 3, the shell 5, and two bodies of foam 4 are provided (FIG. 5). Evidently, also a single body of foam 4 or one or more layers of foam could be used.

The container 3 comprises a body 6 and a collar 7 on which a protrusion 14 is arranged (in this case a single protrusion 14, but the embodiment of the invention can also be used with containers 3 comprising any number of protrusions 14 or recesses 13). At the top of the collar 7 the tubing 2 is attached.

According to the invention, the tubing 2 is placed inside the shell 5 together with the layer of foam 4 and/or body of foam (FIG. 6).

As is apparent, the layer of foam 4 and/or body of foam is interposed between the shell 5 and the tubing 2, preferably such that the layer of foam and/or body of foam 4 completely surrounds the tubing 2 (at least around a rough longitudinal axis of the tubing, but preferably also at the top end portion of the tubing).

The tubing 2 in this example comprises three silicone tubes which protrude from the container 3. The tubing 2 can also comprise one or more sterile connectors and other assorted accessories.

Figure 7:
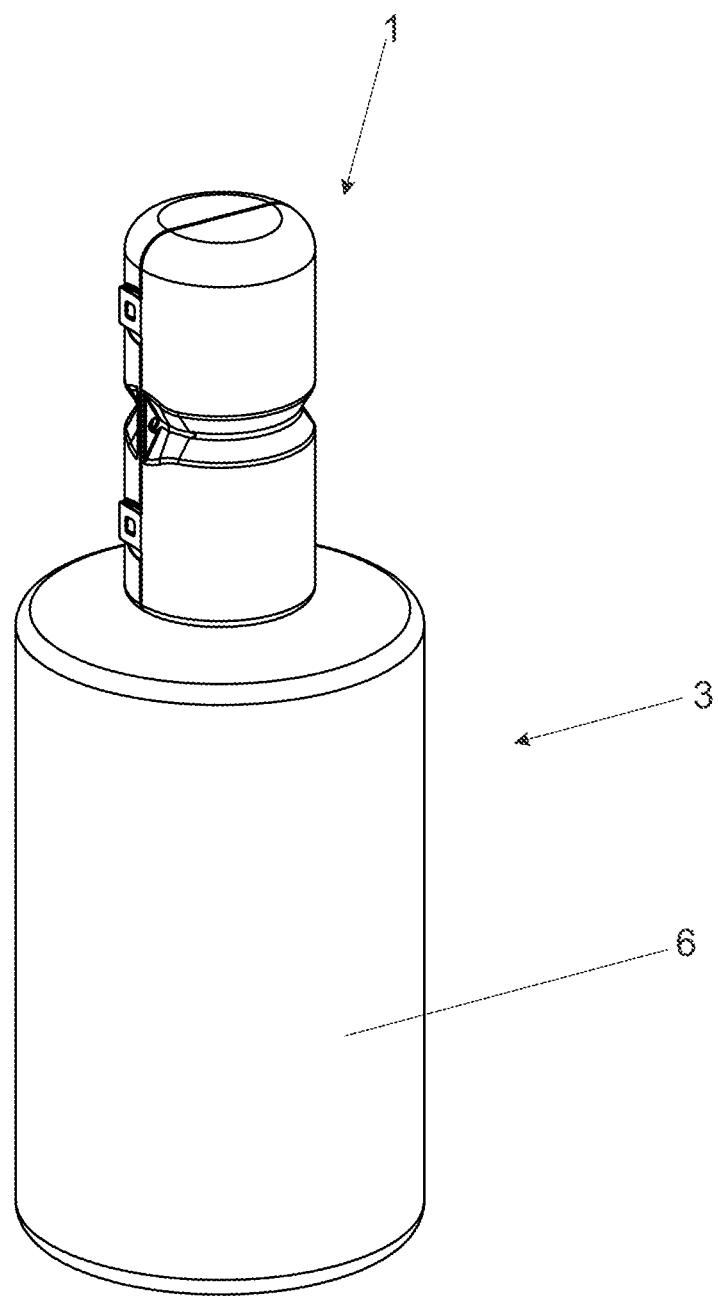
Figure 8:
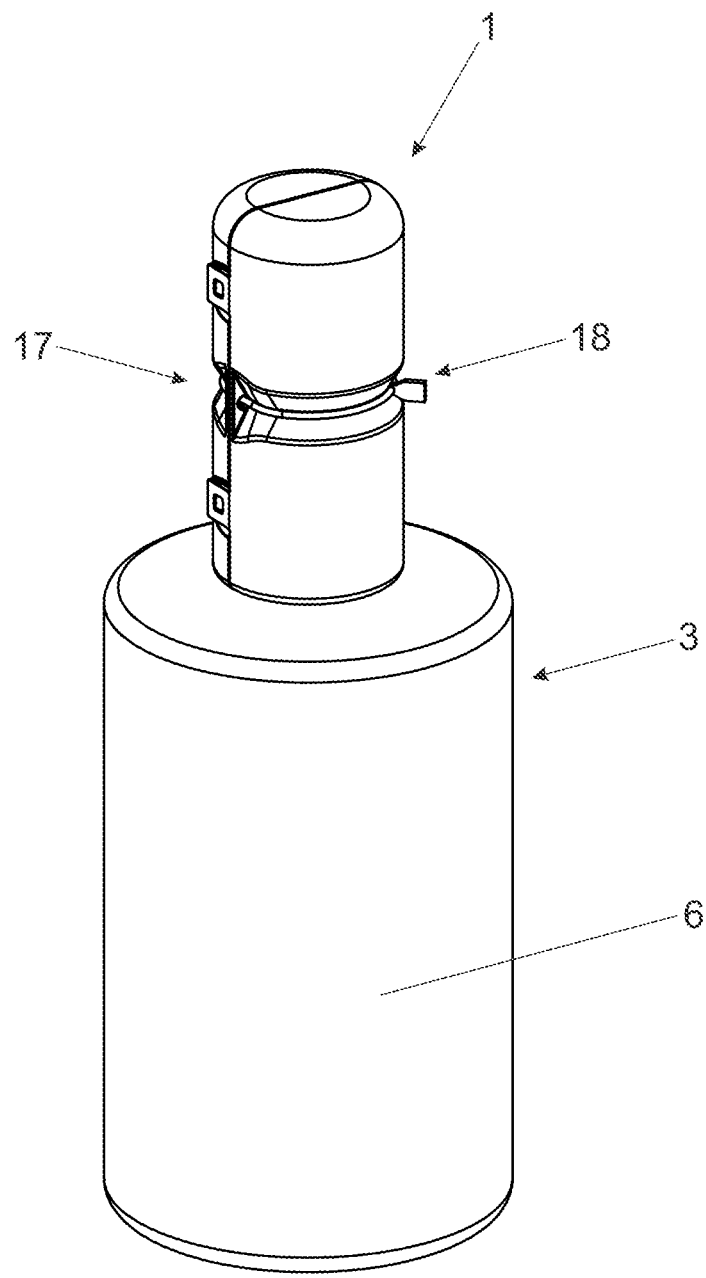

Now closing the shell 5 results in the protrusions 14 engaging with recesses 13 such that the protection device 1 is attached to the container 3 and cannot be easily separated from the same (this is depicted in FIG. 7).

Of course, the locations of the protrusions 13 and the recesses 14 could be interchanged, and the attachment of the shell 5 to the container 3 could analogously be effected in this way.

Once the shell 5 is closed (FIG. 7), the tubing 2 is safely protected inside the layer of foam 4 and/or body of foam as well as the shell 5, while the body 6 of the container 3 is kept free, i.e. outside of the shell. In this way, the tubing 2 is effectively and easily protected without adding to the bulk of the container 2 itself.

Figure 9:
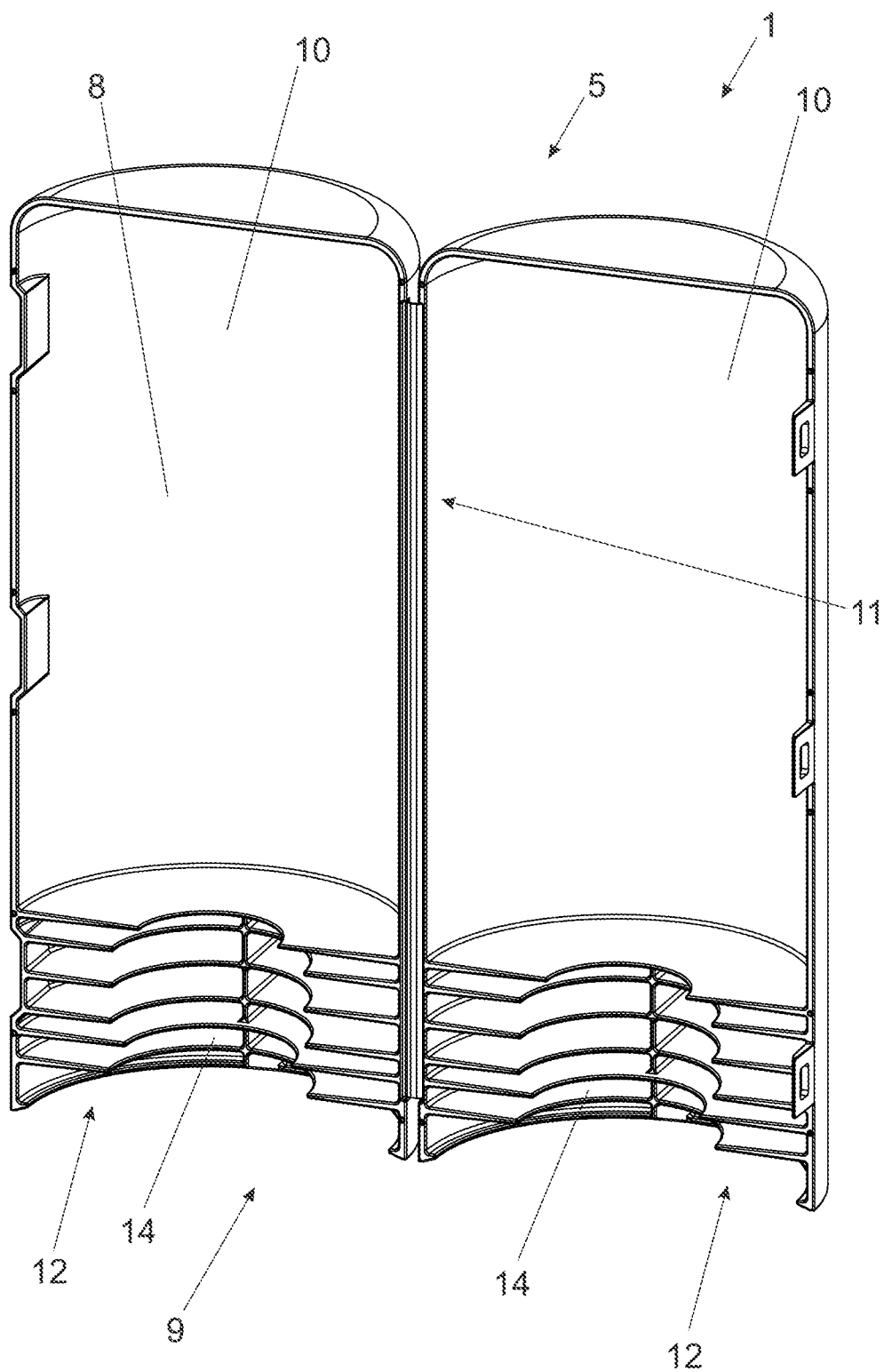
Figure 10:
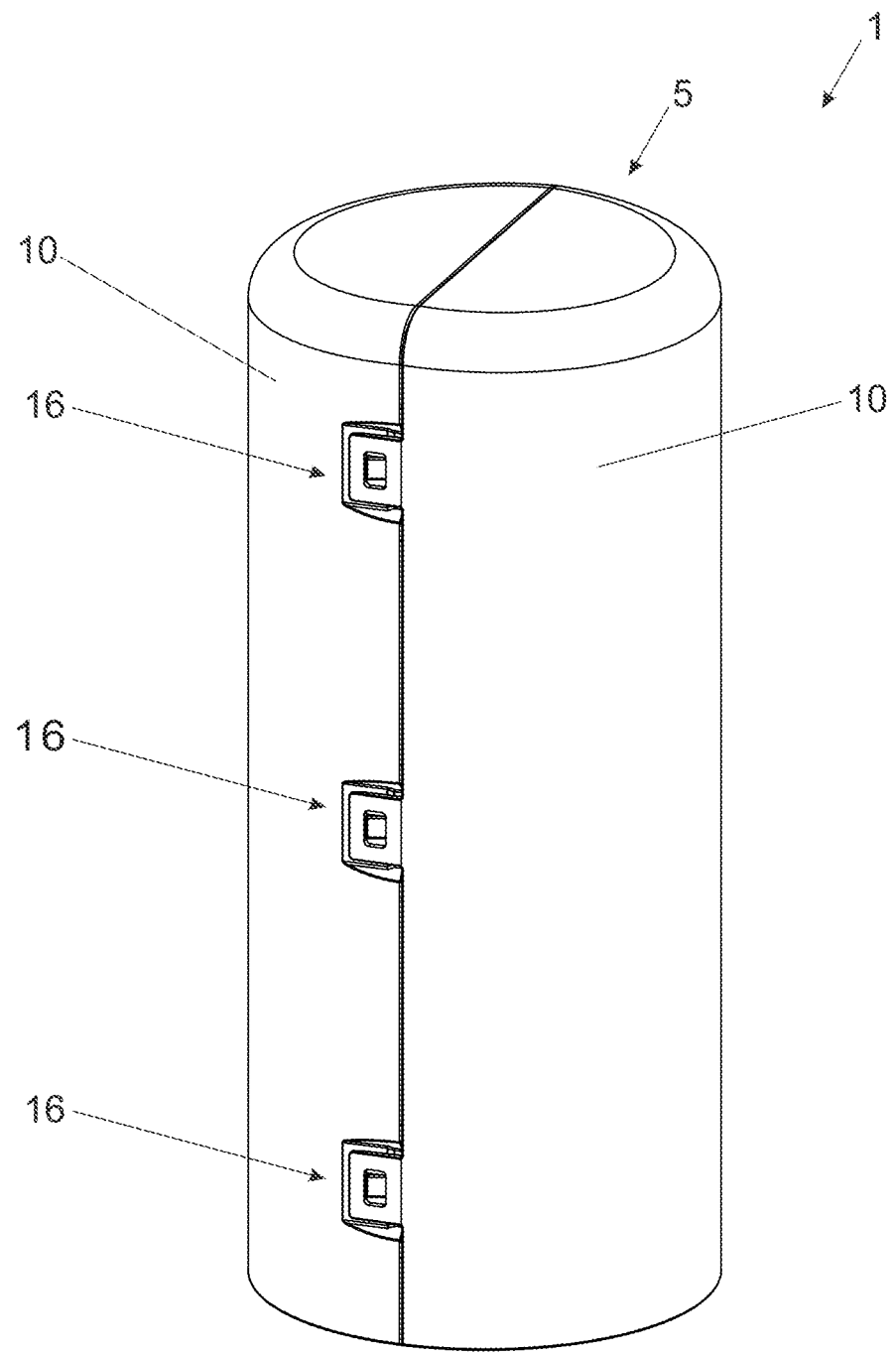

FIGS. 9 and 10 show another embodiment of the protection device 1 according to the invention in an open and a closed configuration respectively, with analogous functional elements as described in connection with the embodiment of FIG. 1.

The invention claimed is:

1. An arrangement comprising:
    a container configured to store a pharmaceutical fluid;
    tubing protruding from the container;
    a protection device for protecting the tubing protruding from the container, the protection device including:
        a shell forming a chamber for surrounding the tubing such that the tubing is arranged entirely inside the shell; and
        an attachment element for attaching the shell to the container such that the tubing is arranged inside the shell; and
    foam between the tubing and the shell of the protection device.

2. The arrangement according to claim 1, wherein the shell comprises two parts connected by a hinge such that the shell can be opened and closed.

3. The arrangement according to claim 2, wherein the two parts are shaped as half shells.

4. The arrangement according to claim 2, wherein the attachment element comprises two attachment element parts, each of the attachment element parts being arranged on a respective one of the two parts of the shell.

5. The arrangement according to claim 4, wherein the two attachment element parts are configured and arranged such that closing the shell simultaneously puts the attachment element into a closed position.

6. The arrangement according to claim 2, wherein the hinge is an integral hinge.

7. The arrangement according to claim 1, wherein the attachment element comprises an engagement element configured to engage a recess and/or a protrusion of the container.

8. The arrangement according to claim 7, wherein the container has a collar at an opening thereof, the recess and/or the protrusion of the container is arranged on the collar.

9. The arrangement according to claim 1, wherein the shell has a substantially cylindrical base shape, the attachment element being arranged at a first base area of the substantially cylindrical base shape, and a second base area of the substantially cylindrical base shape being closed off.

10. The arrangement according to claim 1, wherein the foam is a layer of foam and/or a body of foam arranged in the chamber of the shell.

11. The arrangement according to claim 1, wherein the container is a bottle, and the arrangement is configured to be in a frozen state.

* * * * *